United States Patent
Conti et al.

(10) Patent No.: US 9,387,188 B2
(45) Date of Patent: Jul. 12, 2016

(54) COMPOSITIONS COMPRISING AMINO ACIDS FOR TREATING CHRONIC OBSTRUCTIVE PULMONARY DISEASE

(75) Inventors: Franco Conti, Milan (IT); Isabella Arborio Mella, legal representative, Milan (IT); Edoardo Carlo Maria Conti, legal representative, Milan (IT); Giovanni Federico Maria Conti, legal representative, Milan (IT); Francesco Saverio Dioguardi, Milan (IT)

(73) Assignee: Determinants of Metabolism Research Laboratory S.r.L., Castel San Giovanni (PC) (IT)

( * ) Notice: Subject to any disclaimer, the term of this patent is extended or adjusted under 35 U.S.C. 154(b) by 168 days.

(21) Appl. No.: 13/512,438

(22) PCT Filed: Nov. 26, 2010

(86) PCT No.: PCT/IB2010/055459
§ 371 (c)(1),
(2), (4) Date: Sep. 11, 2012

(87) PCT Pub. No.: WO2011/064755
PCT Pub. Date: Jun. 3, 2011

(65) Prior Publication Data
US 2013/0018080 A1    Jan. 17, 2013

(30) Foreign Application Priority Data
Nov. 27, 2009 (IT) ............... TO2009A0932

(51) Int. Cl.
| | |
|---|---|
| *A61K 31/415* | (2006.01) |
| *A01N 43/50* | (2006.01) |
| *A61K 31/198* | (2006.01) |
| *A61K 45/06* | (2006.01) |

(52) U.S. Cl.
CPC ............. *A61K 31/198* (2013.01); *A61K 45/06* (2013.01)

(58) Field of Classification Search
None
See application file for complete search history.

(56) References Cited

U.S. PATENT DOCUMENTS

| | | |
|---|---|---|
| 2006/0173079 A1 | 8/2006 | Engelen et al. |
| 2007/0010437 A1 | 1/2007 | Dioguardi |
| 2007/0041912 A1 | 2/2007 | Ehrich et al. |
| 2009/0192197 A1 | 7/2009 | Rhee et al. |

FOREIGN PATENT DOCUMENTS

| | | | |
|---|---|---|---|
| EP | 2 080 508 | 7/2009 | |
| WO | WO 02/02092 | 1/2002 | |
| WO | WO02/02092 A2 * | 1/2002 | ........... A61K 31/198 |
| WO | WO 2004/062656 | 7/2004 | |
| WO | WO 2004/093861 | 11/2004 | |
| WO | WO 2005/034932 | 4/2005 | |
| WO | WO 2005034932 A2 * | 4/2005 | ........... A61K 31/198 |

OTHER PUBLICATIONS

Rutten et al. (Clinical Nutrition, Mar. 4, 2008, 27, 408-415).*
International Search Report for PCT/IB2010/055459 mailed Apr. 13, 2011.
Written Opinion of the International Searching Authority mailed Apr. 13, 2011.
M. Engelen et al., Factors Contributing to Alterations in Skeletal Muscle and Plasma Amino Acid Profiles in Patients with Chronic Obstructive Pulmonary Disease, The American Journal of Clinical Nutrition, American Society for Nutrition, vol. 72, Jul. 27, 2000, pp. 1480-1487.
European Patent Office Action dated May 7, 2013, from European Patent Application No. EP 10809044.0.
M. Engelen et al., Factors Contributing to Alterations in Skeletal Muscle and Plasma Amino Acid Profiles in Patients with Chronic Obstructive Pulmonary Disease, The American Journal of Clinical Nutrition, American Society for Nutrition, vol. 72, Jul. 27, 2000, pp. 1480-1487
T. Kutsuzawa et al., "Plasma Branched-Chain Amino Acid Levels and Muscle Energy Metabolism in Patients with Chronic Obstructive Pulmonary Disease" Clinical Nutrition, vol. 28, No. 2, Apr. 1, 2009, pp. 203-208.

* cited by examiner

*Primary Examiner* — Dennis Heyer
*Assistant Examiner* — Daniel M Podgorski
(74) *Attorney, Agent, or Firm* — Nixon & Vanderhye P.C.

(57) ABSTRACT

A composition comprising leucine, isoleucine, valine, threonine and lysine for treating chronic obstructive pulmonary disease.

15 Claims, 4 Drawing Sheets

Fig. 1

| Variables | Placebo Group | | T2 vs T1 | T3 vs T1 | AA Group | | T2 vs T1 | T3 vs T1 | Interaction |
|---|---|---|---|---|---|---|---|---|---|
| pCO$_2$ (mmHg) | T 1 | 46.28±7.6 | | | T 1 | 45.32±6 | | | |
| | T 2 | 46.21±3.88 | ns | ns | T 2 | 46.32±5.22 | ns | p=0.46 | p=0.77 |
| | T 3 | 45.47±4.87 | | | T 3 | 46±3.74 | | | |
| pO$_2$ (mmHg) | T 1 | 60.15±4.88 | | | T 1 | 61.56±8.5 | | | |
| | T 2 | 58.12±4.58 | ns | ns | T 2 | 62.20±6.28 | ns | p=0.01 | p=0.039 |
| | T 3 | 57.14±4.14 | | | T 3 | 66.31±5.89 | | | |
| sO$_2$ (%) | T 1 | 94.32±0.96 | | | T 1 | 94.6±1.86 | | | |
| | T 2 | 93.98±1.71 | ns | ns | T 2 | 92.75±2.76 | ns | p=0.75 | p=0.04 |
| | T 3 | 94±1.73 | | | T 3 | 94±2.42 | | | |
| FEV1 (l/sec) | T 1 | 0.84±0.15 | | | T 1 | 0.90±0.22 | | | |
| | T 2 | 0.78±0.16 | ns | ns | T 2 | 0.90±0.22 | ns | p=0.46 | p=0.58 |
| | T 3 | 0.75±0.15 | | | T 3 | 0.86±0.16 | | | |
| FEV1/FVC (%) | T 1 | 38±11.49 | | | T 1 | 39.62±7.35 | | | |
| | T 2 | 37.61±12.9 | ns | ns | T 2 | 39.5±7.20 | ns | p=0.7 | p=0.89 |
| | T 3 | 36.13±10.33 | | | T 3 | 39.19±7.5 | | | |
| Plasma lactate (μmol/l) | T 1 | 1.73±0.27 | | | T 1 | 1.65±0.70 | | | |
| | T 2 | 1.8±0.35 | ns | ns | T 2 | 1.43±0.30 | ns | p=0.023 | p=0.07 |
| | T 3 | 1.95±0.36 | | | T 3 | 1.3±0.57 | | | |
| FFM (Kg) | T 1 | 39.86±4.82 | | | T 1 | 40.41±4 | | | |
| | T 2 | 39.95±3 | ns | ns | T 2 | 41.56±4.51 | ns | p=0.05 | p=0.05 |
| | T 3 | 39.73±2.78 | | | T 3 | 44±4.53 | | | |
| BW (Kg) | T 1 | 54.38±6.95 | | | T 1 | 53.47±6.53 | | | |
| | T 2 | 54±6.82 | ns | ns | T 2 | 55.4±8.44 | ns | p=0.002 | p=0.006 |
| | T 3 | 53.31±5.77 | | | T 3 | 59±10 | | | |
| LBMI (Kg/m$^2$) | T 1 | 14.91±2 | | | T 1 | 15.34±2 | | | |
| | T 2 | 14.97±1.73 | ns | ns | T 2 | 15.7±1.51 | ns | p=0.07 | p=0.09 |
| | T 3 | 14.89±1.63 | | | T 3 | 16.68±2 | | | |
| BMI (Kg/m$^2$) | T 1 | 20.21±1.80 | | | T 1 | 20.16±1.43 | | | |
| | T 2 | 20±1.65 | ns | ns | T 2 | 20.82±2.34 | ns | p=0.002 | p=0.006 |
| | T 3 | 19.9±1.69 | | | T 3 | 22.26±2.68 | | | |
| Steps (n°) | T 1 | 609.81±454.72 | | | T 1 | 638.8±661.8 | | | |
| | T 2 | 651.94±557.88 | ns | ns | T 2 | 880.20±836.60 | ns | p=0.01 | p=0.0027 |
| | T 3 | 562.88±601.87 | | | T 3 | 1140.53±524.39 | | | |
| Serum protein total (g/l) | T 1 | 61.57±5.15 | | | T 1 | 62.20±2.66 | | | |
| | T 2 | 60.35±5.17 | ns | ns | T 2 | 63.83±3.96 | ns | p=0.041 | p=0.12 |
| | T 3 | 60.94±5.12 | | | T 3 | 65±3.57 | | | |
| Serum albumin (g/l) | T 1 | 33.16±2.71 | | | T 1 | 32.94±3.67 | | | |
| | T 2 | 32.49±3.43 | ns | ns | T 2 | 35.14±3.51 | p=0.001 | p=0.001 | p<.001 |
| | T 3 | 33.28±4.39 | | | T 3 | 37.22±2.86 | | | |
| MMSE (score) | T 1 | 20.19±3.52 | | | T 1 | 19.13±4.6 | | | |
| | T 2 | 19.62±3.59 | ns | ns | T 2 | 19±3.9 | ns | p=0.011 | p=0.011 |
| | T 3 | 19.44±3.68 | | | T 3 | 20.75±3.92 | | | |
| SGRQ (score) | T 1 | 71.44±6.98 | | | T 1 | 72.25±8.52 | | | |
| | T 2 | 72.81±7 | ns | ns | T 2 | 69.56±9.41 | p=0.01 | - | p<0.001 |
| | T 3 | - | | | T 3 | - | | | |

COMPOSITIONS COMPRISING AMINO ACIDS FOR TREATING CHRONIC OBSTRUCTIVE PULMONARY DISEASE

This application is the U.S. national phase of International Application No. PCT/IB2010/055459 filed 26 Nov. 2010 which designated the U.S. and claims priority to IT TO2009A000932 filed 27 Nov. 2009, the entire contents of each of which are hereby incorporated by reference.

FIELD OF THE INVENTION

The present invention relates to compositions comprising amino acids that are suitable for treating chronic obstructive pulmonary disease in mammals.

TECHNOLOGICAL BACKGROUND

Chronic obstructive pulmonary disease (COPD) is a disease of the respiratory apparatus, characterized by an irreversible obstruction of the airways, of a degree that varies according to the gravity. Chronic obstructive pulmonary disease is usually progressive and is associated to a state of chronic inflammation of the pulmonary tissue. The long-term consequence is an outright remodelling of the bronchi, which causes a considerable reduction in respiratory capacity.

COPD frequently causes a change in body conformation, consisting in a loss of weight and of muscle mass. The prevalence of underweight is 35-60% in COPD of a moderate-to-severe type, whilst the prevalence of reduction of muscle mass is approximately 20% in clinically stable forms. Alterations of body composition have a negative impact on organs and body districts of the patient, ultimately reducing their respiratory and peripheral-musculature function, motor autonomy, capacity of defense against infections, cognitive functions, state of health, and survival, irrespective of the degree of obstruction of the airways. At 10 years from onset of chronic obstructive pulmonary disease the survival rate is 40%.

Numerous factors concur in alterations of body composition, from inadequacy of the caloric intake, especially in periods of acute exacerbation of the disease, to alterations of protein balance on account of the prevalence of protein catabolism over the processes of protein synthesis.

Given the extent of the prognosticated reduction in vital functions and life expectancy, numerous studies have investigated into the best strategy to enable prevention, correction or limitation of weight loss, above all loss in muscle mass, induced by COPD, and investigations are still in progress. Fundamentally, these studies have adopted three approaches: i) nutritional intervention; ii) pharmacological intervention; iii) integrated nutrition-rehabilitation intervention.

All three approaches present, however, serious limits.

The nutritional supplementation based upon an incremented protein-caloric intake improves body weight and respiratory-musculature function. However, clinical practice highlights the fact that patients with severe COPD are highly unlikely to be able to introduce 2300-2500 kcal each day with the food.

Pharmacological interventions have demonstrated very limited results. For example, the use of megestrol, a progestational molecule with the effect of stimulating the appetite, induces an increase in weight due to increase in fat mass but not in lean (muscle) mass. Anabolic steroids (growth hormone, testosterone, stanazolol, oxandrolone) induces minor increases in fat-free mass, but no clear improvement of the functional and pulmonary state.

Nutritional supplementation with approximately 600 kcal, when inserted in a programme of respiratory rehabilitation of the duration of 8 weeks, is able to improve weight, muscle mass, maximum respiratory pressure, muscular strength, capacity for physical exercise in underweight patients with COPD. However, there exists the major limit that many patients do not have the possibility of access to rehabilitation carried out in hospital regime or do not manage to carry out intense physical exercise.

SUMMARY OF THE INVENTION

The aim of the present invention is to indicate a therapeutic approach to malnutrition in COPD that will enable the drawbacks of the prior art to be overcome. Said aim is achieved thanks to the use of essential amino-acid-based compositions, designed for oral administration, which have the characteristics recalled in the ensuing claims.

The rationale for the use of essential amino acids is based upon scientific evidence from studies conducted on animals and on humans: amino acids regulate the protein turnover both by acting on the protein metabolism and on the anaerobic metabolism aimed at the production of energy essential for protein synthesis and by enhancing the biological activity of anabolic hormones such as insulin and IGF-1.

The compositions according to the invention are particularly useful for the treatment of disorders determined by conditions of severe COPD, and comprise a mixture of free amino acids suitable for a protracted use in time.

The inventors have in fact found that the supplementation of free amino acids, in particular essential amino acids, is surprisingly effective in the treatment of outpatients with COPD and with a severe respiratory picture (FEV1<40% of the theoretical value, hypercapnaemia, hypoxaemia), inducing significant changes in terms of increase in body weight and composition, reduction in anaerobic metabolism (evidenced by the reduction of concentration of lactic acid in the blood), increase in blood oxygen tension, increase in motor autonomy, reduction in cognitive disorders, improvement of perception of health.

Consequently, the present invention regards amino-acid-based compositions for the treatment of patients affected by COPD, which have as main active ingredients the branched amino acid leucine in combination with at least one of, and preferably both of, the branched amino acids isoleucine and valine. In a particular embodiment, the present invention concerns compositions comprising as main active ingredients the branched amino acids leucine, isoleucine, and valine in combination with at least one of, and preferably both of, threonine and lysine.

The compositions according to the invention are preferably envisaged for chronic or prolonged use, namely with a administration preferably protracted for at least 90 days (3 months).

An advantage linked to the use of the compositions described herein lies in the high tolerability of the composition, which can be administered on a prolonged basis. Another substantial advantage of the compositions forming the subject of the invention is represented by the simplicity of use thereof for the patients treated. The compositions are preferentially produced, with or without excipients, according to known techniques, in formulations suitable for oral administration. In a preferred embodiment, the compositions described herein have a pH in aqueous solution comprised between 6.5 and 8.5, with or without excipients suited for the preparation of tablets, capsules, powders, etc., via which it is intended to obtain a pharmacological form suited for oral use.

The compositions of amino acids according to the invention hence prove very useful for those patients affected by COPD who are unable to undergo rehabilitation, for example on account of difficulty of access to hospital rehabilitation centres, or else are unable to carry out intense activities of physical exercise, for example on account of complications, seriousness of the clinical conditions, advanced age.

Another advantage linked to the use of the compositions described herein lies in the fact that the use of amino acids in free form enables production of said compositions at a very contained industrial cost as compared to drugs of synthesis, via processes in themselves known and widely used in the sector of the preparation of compositions based on free amino acids. The scope of application of the invention can on the other hand be extended to amino acids obtained via genetic engineering or with any other artificial method.

BRIEF DESCRIPTION OF THE DRAWINGS

The invention will now be described in detail, purely by way of non-limiting example, also with reference to the annexed figures, wherein:

FIG. 1 is a table that compares a series of variables found in a control group CA, treated with placebo, and a group AA treated with a mixture of amino acids according to the invention;

DETAILED DESCRIPTION OF PREFERRED EMBODIMENTS OF THE INVENTION

Figure 2:
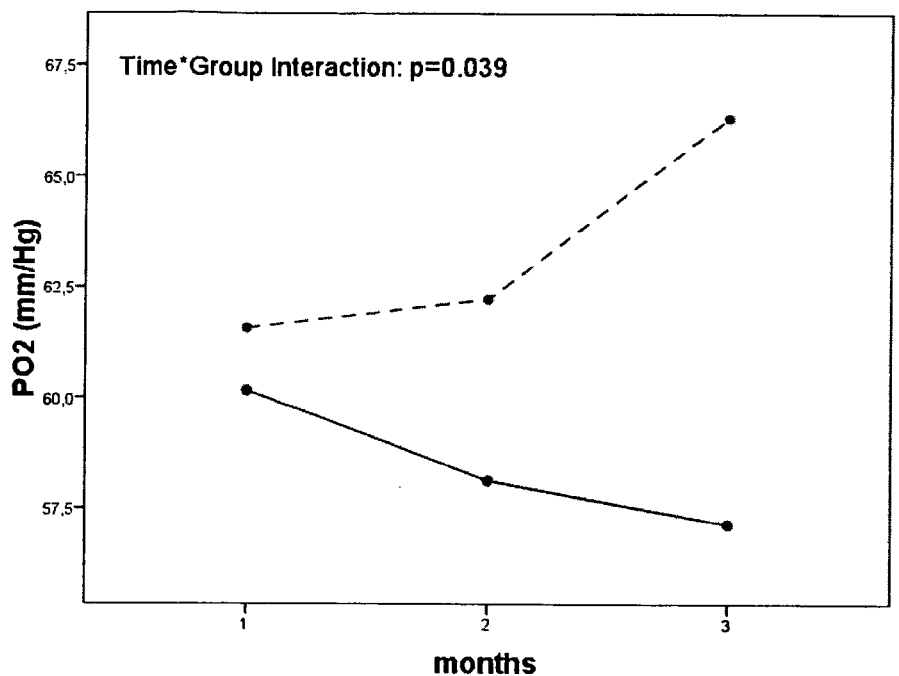
FIGS. 2 to 7 are diagrams that express graphically the evolution in time of some of the variables appearing in FIG. 1, for the two groups forming the subject of the study.

The compositions according to the invention comprise, as main active ingredients, the branched amino acid leucine in combination with at least one of, and preferably both of, the branched amino acids isoleucine and valine. The preferred molar ratios of isoleucine and valine, with respect to one mole of leucine, are the following:

isoleucine: from 0.2 to 0.7, preferably from 0.4 to 0.6;
valine: from 0.2 to 0.8, preferably from 0.4 to 0.7.

The inventors were able to verify that the activity of the mixtures is increased by adding to the branched amino acids at least one of, and preferably both of, the amino acids threonine and lysine. In greater detail, the preferred molar ratios of these amino acids, with respect to one mole of leucine, are the following:

threonine: from 0.15 to 0.50, preferably from 0.2 to 0.45;
lysine: from 0.15 to 0.60, preferably from 0.3 to 0.55.

In particular, at present, the studies conducted by the inventors have demonstrated how the most effective compositions are those in which, setting at 1 the sum of leucine, isoleucine and valine, in the stoichiometric ratios identified above, the sum of threonine and lysine is comprised between 0.10 and 0.50, once again on the basis of the molar weight, and preferably between 0.25 and 0.45.

The studies conducted by the inventors have further demonstrated that said compositions prove more active in the presence of one or more further essential amino acids selected from among histidine, phenylalanine, methionine, and tryptophan. Setting at 1 the sum of leucine, isoleucine, valine, threonine and lysine, the total amount of the further essential amino acids may range between 0.02 to 0.25, preferably from 0.05 to 0.15, once again understood as molar ratio.

The sum of the quantities of threonine and lysine, once again on the basis of the molecular weight, is preferably less than the sum of the individual quantities of the branched amino acids used, but greater than the sum of the quantities of the further essential amino acids used in the mixtures. In addition, once again preferably and on the basis of molecular weight:

the quantity of lysine is less than individual quantities of the branched amino acids, but greater than the individual quantities of each of the further essential amino acids used in the mixtures (and hence also greater than the sum of the individual quantities of said further essential amino acids, without considering threonine amongst these);

the quantity of threonine is less than the individual quantities of lysine and of the branched amino acids, but greater than the individual quantities of the further essential amino acids used in the mixtures, and much more preferably greater than the sum of the individual quantities of the further essential amino acids.

In the case of use of methionine, the activity of the mixtures can be further improved by envisaging insertion in the composition also of the non-essential amino acid cystine (and/or cysteine), in a quantity in moles at least equal to that of methionine, and preferably comprised between 150% and 350% of methionine.

In addition to the amino acids indicated above, the compositions described herein can comprise also the non-essential amino acid tyrosine, the optimal quantity of which will be comprised between 15% and 50%, preferably between 20% and 35%, of the quantity in moles of phenylalanine.

Even though the compositions may possibly comprise amino acids other than to those indicated above, these will be in overall quantity not greater than 20% of the total amount of active ingredients, and/or not greater than 10% for each individual other amino acid (once again in molar weight). Furthermore, in particular, for the purposes of preparation of the compositions according to the invention, the amino acids serine, proline, glycine, alanine, glutamic acid, and arginine, are preferentially avoided, since they may prove couterproductive or even harmful in some cases.

The amounts administered of the compositions according to the invention are preferably comprised between approximately 4 g/day and approximately 12 g/day, more preferably, approximately 8-10 g/day.

The amino acids used in the experimentation that has led to the identification of the ratios indicated are those of a laevorotatory type, which correspond to those present in nature and are hence to be considered the preferred active form. However, the inventors have verified that also the racemic form can explicate the same activity, even though to a proportionally lesser extent. In the framework of the present invention have to be considered of course included are also the active derivatives of the amino acids indicated, in particular their salts.

Further specifications, in terms of quantities and ratios between the various amino acids envisaged by the compositions according to the invention are contained in the annexed claims, which form an integral part of the technical teaching provided herein in relation to the invention.

Even though expressed on the basis of molecular weight (i.e., in moles), the ratios indicated are applicable, in general terms, also in the case of calculation on the basis of the weight in grams of the various amino acids indicated (bearing in mind, however, that the quantity of lysine, expressed in grams, may then be greater than the individual quantities of isoleucine and valine).

We shall now provide, by way of non-limiting examples, demonstration of the effects produced in mammals by the chronic administration via oral route of a composition of free amino acids obtained according to the invention.

1. MATERIALS AND METHODS

Thirty-two patients (25 males) affected by serious COPD (FEV1/FVC<40%), age 75±7 years, were randomized into two groups: a control group CA, treated with placebo, and a group AA treated with 8 g/day of a mixture of amino acids (n=16; group CA: 11 males and 5 females; group AA: 14 males and 2 females). At the start of the study (T1), after a month from the start of the study (T2), and after three months from the start of the study (T3), variables were measured, such as the body weight, the fat-free mass (BIA method), the concentration of plasma lactate, the blood tension of oxygen ($O_2$) and carbon dioxide ($CO_2$), physical activity, cognitive function, perception of health.

Descriptive statistics (mean±standard deviation) was applied to all the variables analysed. The baseline characteristics (time T1) of group CA treated with placebo with respect to group AA treated with the amino acids were compared by means of the Student's t-test for unpaired data. A method of analysis of the variance for repeated measurements with a factor (Group) was applied for evaluating the evolution in time of all the variables analysed. The statistical significance was expressed as the value of the Time*Group interaction, by testing the different evolutions between patients belonging to group CA or to group AA. The Bonferroni post-hoc test was applied to evaluate subsequently differences between points in time within and between the curves.

Following upon randomization, the cachectic patients of the two groups CA and AA proved to have characteristics substantially similar in terms of pulmonary function, body weight and composition, muscular-skeletal metabolism, type of physical activity, cognitive function, and perception of health.

The patients of group AA were supplemented with 8 g/day of a mixture of amino acids in accordance with the principles indicated previously. The composition of the mixture appears in Table 1 below.

TABLE 1

| Amino acid | Molec. weight* | g/100 g | % over tot. | % over group |
|---|---|---|---|---|
| L-Leucine | 131.17 | 31.2500 | 31.25% | 50.00% |
| L-Isoleucine | 131.17 | 15.6250 | 15.63% | 25.00% |
| L-Valine | 117.15 | 15.6250 | 15.63% | 25.00% |
| Branched amino acid | | 62.5000 | 62.50% | 100.00% |
| L-Lysine | 146.19 | 16.2500 | 16.25% | 65.00% |
| L-Threonine | 119.12 | 8.7500 | 8.75% | 35.00% |
| lysine + threonine | | 25.0000 | 25.00% | 100.00% |
| L-Histidine | 155.16 | 3.7500 | 3.75% | 46.88% |
| L-Phenylalanine | 165.19 | 2.5000 | 2.50% | 31.25% |
| L-Methionine | 149.21 | 1.2500 | 1.25% | 15.63% |
| L-Tryptophan | 204.23 | 0.5000 | 0.50% | 6.25% |
| further essential amino acid | | 8.0000 | 8.00% | 100.00% |
| L-Tyrosine | 181.19 | 0.7500 | 0.75% | |
| L-Cystine | 240.30 | 3.7500 | 3.75% | |
| Total composition | | 100.0000 | 100.00% | |

*from "Amino Acid, Nucleic Acids & Related Compounds - Specification/General Tests", 8th Edition, Kyowa Hakko Kogyo Co., Ltd.

In Table below 2 the quantities in grams of the composition appearing in Table 1 are expressed on the basis of molecular weight, i.e., in moles.

TABLE 2

| Amino acid | Molec. weight | Mol | % over tot. | % over group |
|---|---|---|---|---|
| L-Leucine | 131.17 | 0.23824 | 31.97% | 48.55% |
| L-Isoleucine | 131.17 | 0.11912 | 15.98% | 24.27% |
| L-Valine | 117.15 | 0.13338 | 17.90% | 27.18% |
| Branched amino acid | | 0.49074 | 65.85% | 100.00% |
| L-Lysine | 146.19 | 0.11116 | 14.92% | 60.21% |
| L-Threonine | 119.12 | 0.07346 | 9.86% | 39.79% |
| lysine + threonine | | 0.18461 | 24.77% | 100.00% |
| L-Histidine | 155.16 | 0.02417 | 3.24% | 48.21% |
| L-Phenylalanine | 165.19 | 0.01513 | 2.03% | 30.19% |
| L-Methionine | 149.21 | 0.00838 | 1.12% | 16.71% |
| L-Tryptophan | 204.23 | 0.00245 | 0.33% | 4.88% |
| further essential amino acid | | 0.05013 | 6.73% | 100.00% |
| L-Tyrosine | 181.19 | 0.00414 | 0.56% | |
| L-Cystine | 240.30 | 0.01561 | 2.09% | |
| Total composition | | 0.74522 | 100.00% | |

As may be noted from Table 1, the weight ratios between leucine, isoleucine and valine are preferably 2:1:1. From Table 1 and from Table 2 it may moreover be noted how the individual quantities (weight in grams or in moles) of histidine, phenylalanine, methionine and tryptophan are preferentially decreasing (i.e., histidine is in an amount greater than phenylalanine, which is in an amount greater than methionine, which is in an amount greater than tryptophan), and the quantity (in weight, in grams, or in moles) of cystine (and/or cysteine) is preferably greater than that of tyrosine.

2. RESULTS

The evolution in time of the variables analysed at the end of the study show how the patients of group AA, unlike those of group CA, progressively improved their nutritional state, muscular metabolism, $pO_2$, daily physical activity, cognitive capacity, and perception of health. The values of the variables analysed, for the two groups CA and AA are compared in tabular form in FIG. 1, where:
  data expressed as mean±standard deviation;
  statistical analysis: Anova test;
  T1=base; T2=after one month; T3=after three months;
  $pCO_2$=partial pressure of carbon dioxide; $pO_2$=partial pressure of oxygen; $sO_2$=saturation of oxygen; FEV1=forced expiratory volume in 1 second; FVC=forced vital capacity: FFM=fat-free mass; BW=body weight; LBMI=lean body mass index; BMI=body mass index; MMSE="Mini Mental State Examination" test; SGRQ=St. George respiratory questionnaire.

Figure 3:
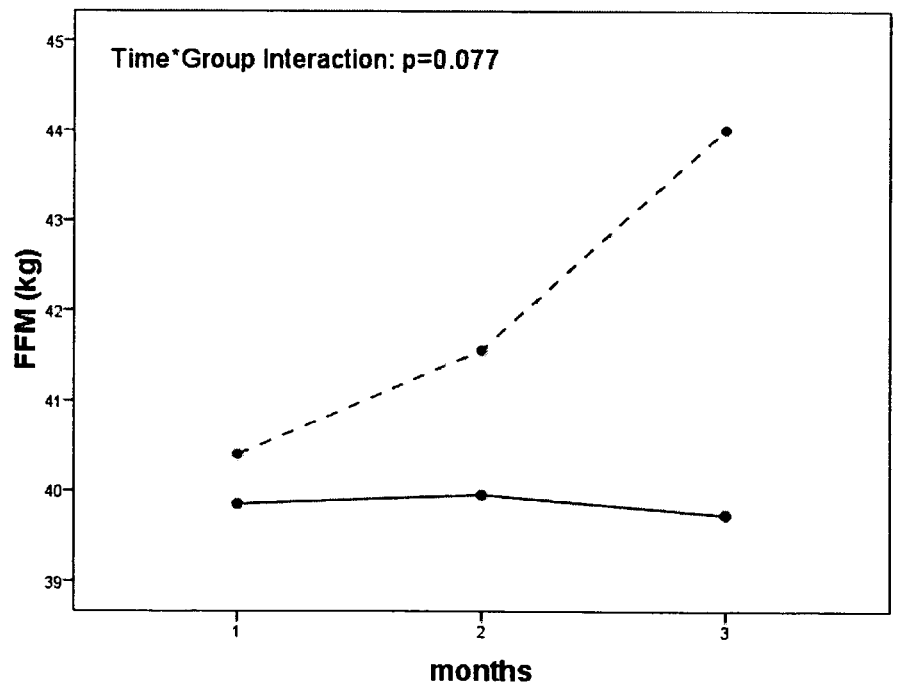
Figure 4:
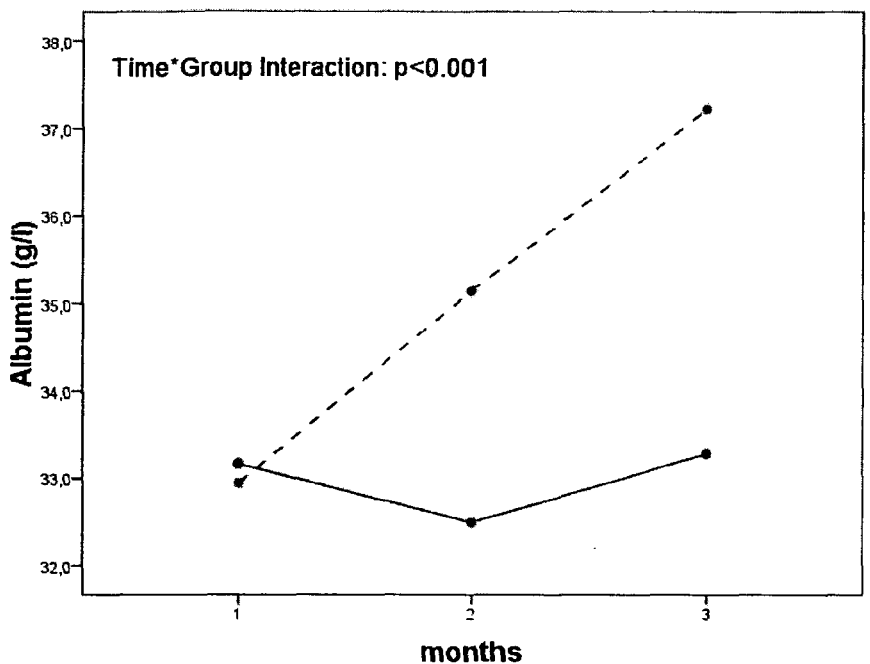
Figure 5:
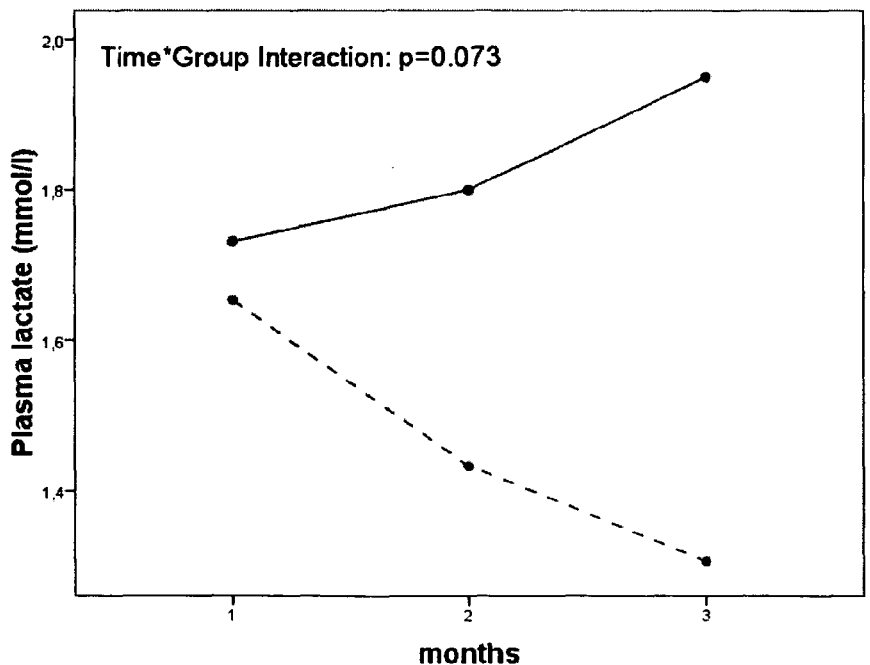
Figure 6:
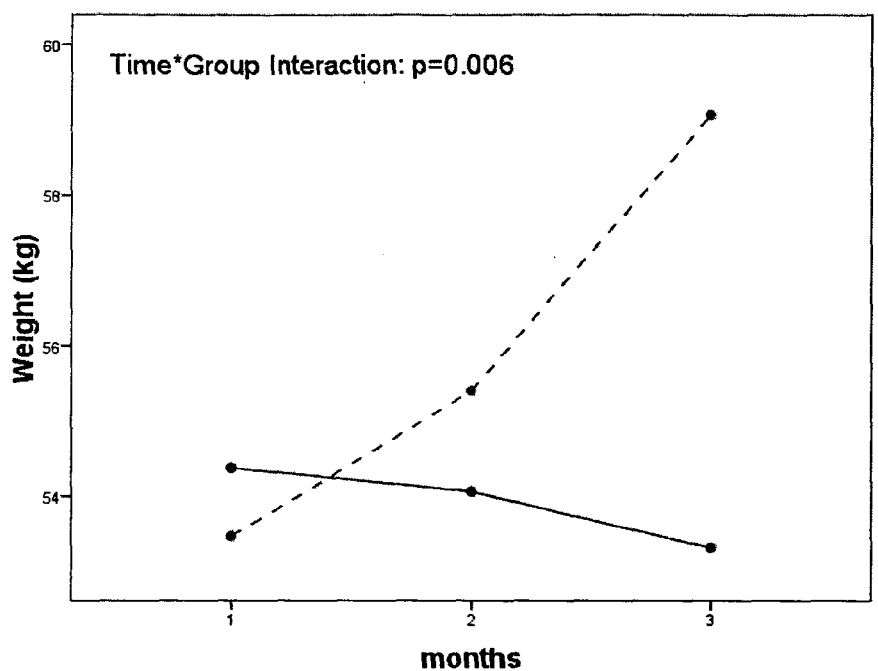
Figure 7:
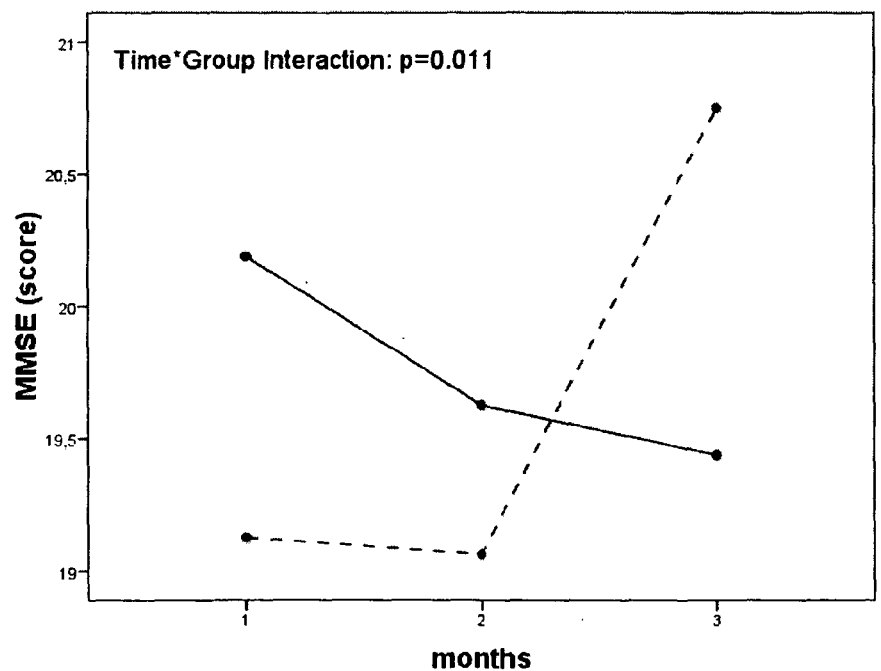

The evolution in time of some of the variables analysed for the two groups are moreover compared in graphic form in FIGS. 2-7, where:
  months=months;
  Time*Group Interaction=Time*Group interaction;
  solid-line curves=group CA; dashed-line curves=group AA;
  Albumin=Albumin; Plasma lactate=Plasma lactate; Weight=Weight From an examination of the figures it may be noted, for example, how at time T3 the patients of group AA presented a decided increase, with respect to the baseline values, both in the body weight (+6 kg, +11%) and in fat-free mass (+3.6 kg; +8.9%), as well as reduced levels of plasma lactate (from 1.6±0.7 μmol/l to 1.3±0.6 μmol/l). Furthermore, altogether unexpectedly, at time T3 there was found a decided increase, with respect to the baseline values, of the blood oxygen tension (+4.6 mmHg; +75%). It should be noted how the improvement of $pO_2$ was not associated to a concomitant increase in $pCO_2$. At time T3, associated moreover to supplementation of amino acids was an increased physical autonomy: the variable regarding the daily physical activity (number of steps) improved by 80% as compared to the baseline value. The visceral protein synthesis (albumin) increased in the patients of group AA from the baseline value of approximately 32.7 g/l to that of 37 g/l (+4.3 g/l). The study also revealed that in the patients of group AA both the cognitive dysfunctions and the negative perception of the state of health were reduced significantly.

The study consequently shows that the supplementation of amino acids in cachectic patients affected by COPD is associated to an improvement in weight, body composition, peripheral muscular anaerobic metabolism, $pO_2$, daily physical activity, cognitive function, and perception of health.

2.1 Body Composition

The increase of 3.6 kg in FFM following upon supplementation with amino acids is surprising, if compared with the gain usually obtainable after 8 weeks of pulmonary rehabilitation of patients (on average 1.1 kg in FFM). The increase in the body weight (+6 kg) is decidedly greater than that resulting from previous investigations based upon the use of megestrol (+3.2 kg after 8 weeks of 800 mg/day of megestrol). However, megestrol principally increases the fat mass and not the muscular tissue.

The mechanisms underlying the effects of the essential amino acids are to be deemed both direct and indirect. The essential amino acids directly stimulate protein synthesis and inhibit proteolysis in various tissues, amongst which skeletal muscles and the liver. The activity of the essential amino acids in these districts probably explains the improvement both in FFM and in albumin synthesis. Protein synthesis promoted by the essential amino acids is independent of insulin, which constitutes an important aspect for those COPD patients who exhibit resistance to insulin. In addition, stimulation of protein anabolism by the essential amino acids induces benefits in cachectic patients with reduced levels of circulation of anabolic hormones, such as testosterone, growth hormone, and somatomedine (insulin-like growth factor or IGF-1).

2.2 Muscle Metabolism

The study shows how the supplementation of essential amino acids is associated to a significant reduction in plasma lactate, whilst in patients treated with placebo the acid concentration is worsened.

The improvement in the formation of lactate can be an effect of the essential amino acids on the muscular metabolism since they can stimulate the production of energy aerobically, both directly, entering into the aerobic cycle, as alternative substrate, and indirectly, shifting to the right the lactate-pyruvate reaction. In this way, the essential amino acids, by reactivating aerobic metabolism, overcome blockage of aerobic oxidation of glucose caused by pro-inflammatory cytochines.

2.3 Daily Physical Activity

The study shows the progressive improvement in daily physical activity of the patients supplemented with essential amino acids even though the physical autonomy remains limited. The total number of steps taken each day by the patients of group AA was approximately 1140 after three months of supplementation (in comparison with 638 of the baseline value at time T1).

Improvement in the motor activity can be ascribed to various factors, amongst which the improvement of the nutritional state, aerobic metabolism, and body anabolism (albumin). These factors can also improve the motivation of the patient in regard to physical activity. An important factor that improves physical activity is the increase in muscular strength induced by essential amino acids.

2.4 Blood Oxygen Tension

The progressive improvement of $pO_2$ following upon the supplementation with amino acids is surprising. A possible explanation is that the improvement in $pO_2$ is due to the influence of amino acids on cardiac function, with improvement of the pulmonary blood flow/distribution.

An improved $pO_2$ can be crucial for the evolution of the state of health of COPD patients in so far as it reduces the stimulus to the production of cytochines and reduces the release of interleuchin 1 and of tumour-necrosis factor-alpha. The reduction of chronic hypoxaemia also probably contributes to the increase in FFM and body weight in the patients.

2.5 Cognitive Capacity and Perception of Health

Improvements in cognitive capacity associated to the use of essential amino acids can be ascribed both to an improved $pO_2$ and to an increased availability at the cerebral level of amino acids precursors of neurotransmitters. The increase in the blood oxygen tension increases cerebral perfusion, which, instead, is reduced by chronic hypoxia. The essential amino acids used in the study contain numerous precursors of the cerebral neurotransmitters that play an important role in cognitive capacities, motor functions, and mood. In particular, norepinephrine, dopamine, and epinephrine derive from tyrosine, serotonin from tryptophan, acetylcholine from methionine, histamine from histidine.

Improvement in the perception of health of the patients is to be deemed an effect of the increased body weight and of FFM, of corporeal anabolic orientation (synthesis of total proteins and albumin), improved $pO_2$, and reduction of cognitive deterioration.

The improvement of cognitive functions and perception of health have important clinical consequences, which include improvement of compliance of the patients to treatment and maintenance of their independence over time.

3. CONCLUSIONS

The documented wide-ranging improvement induced by essential amino acids highlights their plurisystemic effect and their versatility, rendering the compositions according to the invention a valid instrument for treating chronic obstructive pulmonary disease and particularly for treating malnutrition deriving from said pathological condition.

The invention claimed is:
1. A method for treating chronic obstructive pulmonary disease in a subject, comprising
 administering to the subject a therapeutically effective amount of a composition comprising
  leucine,
  isoleucine,
  valine,
  threonine,
  lysine,
  histidine,
  phenylalanine,
  methionine,
  tryptophan,
  tyrosine, and
  cystine wherein said administering increases blood oxygen tension of the subject,
wherein
the molar ratio leucine:isoleucine is in the range of 1:0.2-0.7, and/or
the molar ratio leucine:valine is in the range of 1:0.2-0.8,
the molar ratio leucine:threonine is in the range of 1:0.15-0.50, and/or
the molar ratio leucine:lysine is in the range of 1:0.15-0.60,
for an overall amount of leucine, isoleucine, valine, threonine and lysine equivalent to one mole, histidine, phenylalanine, methionine and tryptophan are in an overall molar ratio with respect to leucine, isoleucine, valine, threonine and lysine between 0.02 and 0.25, and
wherein the composition is free of arginine, serine, proline, glycine, alanine, and glutamic acid.

2. The method according to claim 1, wherein the composition is administered orally.

3. The method according to claim 1, comprising administering the composition chronically for a protracted period of time.

4. The method according to claim 1, wherein the weight ratio leucine:isoleucine:valine is substantially equal to 2:1:1.

5. The method according to claim 1, wherein for an overall amount of leucine, isoleucine and valine equivalent to one mole, threonine and lysine are in an overall molar ratio with respect to leucine, isoleucine and valine between 0.10 and 0.50 (1:0.10-0.50).

6. The method according to claim 1, wherein the methionine:cystine molar ratio is in the range 1:1-3.5.

7. The method according to claim 1, wherein the phenylalanine:tyrosine molar ratio is in the range 1:0.15-0.5.

8. The method according to claim 1, wherein the composition is administered in an amount between about 4 and about 12 g/day.

9. The method according to claim 1, wherein
the molar ratio leucine:isoleucine is in the range of 1:0.4-0.6, and/or
the molar ratio leucine:valine is in the range of 1:0.4-0.7.

10. The method according to claim 1, wherein
the molar ratio leucine:threonine is in the range of 1:0.20-0.45, and/or
the molar ratio leucine:lysine is in the range of 1:0.30-0.55.

11. The method according to claim 1, wherein for an overall amount of leucine, isoleucine and valine equivalent to one mole, threonine and lysine are in an overall molar ratio with respect to leucine, isoleucine and valine between 0.25 and 0.45 (1:0.25-0.45).

12. The method according to claim 1, wherein for an overall amount of leucine, isoleucine, valine, threonine and lysine equivalent to one mole, histidine, phenylalanine, methionine and tryptophan are in an overall molar ratio with respect to leucine, isoleucine, valine, threonine and lysine between 0.05 and 0.15 (1:0.05-0.15).

13. The method according to claim 1, wherein the composition is administered in an amount between about 8 and about 10 g/day.

14. The method according to claim 1, wherein the phenylalanine:tyrosine molar ratio is in the range 1:0.2-0.35.

15. A method for treating chronic obstructive pulmonary disease in a subject, comprising
administering to the subject a therapeutically effective amount of a composition comprising the following active ingredients:
branched amino acid leucine in combination with branched chain amino acids isoleucine and valine,
essential amino acids threonine and lysine,
amino acids histidine, phenylalanine, methionine, tryptophan, tyrosine, and cystine,
wherein said administering increases blood oxygen tension of the subject,
wherein the composition is free of arginine, serine, proline, glycine, alanine, and glutamic acid,
wherein the weight ratios between leucine, isoleucine, and valine are about 2:1:1,
wherein histidine is in a weight amount greater than phenylalanine, which is in a weight amount greater than methionine, which is in a weight amount greater than tryptophan,
wherein cystine is in a weight amount greater than that of tyrosine.

* * * * *